(12) United States Patent
Mladenov et al.

(10) Patent No.: US 10,524,843 B2
(45) Date of Patent: Jan. 7, 2020

(54) ROTATION SHAFT FOR A ROD REDUCER

(71) Applicant: K2M, Inc., Leesburg, VA (US)

(72) Inventors: Kiril Mladenov, Sankt Augustin (DE); Brittany Harwell, Warrenton, VA (US); Brandon Moore, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 17 days.

(21) Appl. No.: 15/586,665

(22) Filed: May 4, 2017

(65) Prior Publication Data

US 2017/0319246 A1 Nov. 9, 2017

Related U.S. Application Data

(60) Provisional application No. 62/332,679, filed on May 6, 2016.

(51) Int. Cl.
*A61B 17/70* (2006.01)

(52) U.S. Cl.
CPC ...... *A61B 17/7086* (2013.01); *A61B 17/7085* (2013.01)

(58) Field of Classification Search
CPC .... A61B 17/7086–7088; A61B 17/7083–7085
See application file for complete search history.

(56) References Cited

U.S. PATENT DOCUMENTS

| | | |
|---|---|---|
| 2,248,054 A | 7/1941 | Becker |
| 3,604,487 A | 9/1971 | Gilbert |
| 4,263,899 A | 4/1981 | Burgin |
| 5,020,519 A | 6/1991 | Hayes et al. |
| 5,364,397 A | 11/1994 | Hayes et al. |
| 5,420,751 A | 5/1995 | Burns |
| 5,431,658 A | 7/1995 | Moskovich |
| 5,466,243 A | 11/1995 | Schmieding et al. |
| 5,529,571 A | 6/1996 | Daniel |
| 5,685,826 A | 11/1997 | Bonutti |
| 5,720,751 A | 2/1998 | Jackson |

(Continued)

FOREIGN PATENT DOCUMENTS

| | | |
|---|---|---|
| EP | 2777571 A1 | 9/2014 |
| FR | 2985166 A1 | 7/2013 |
| WO | 2016/175885 A1 | 11/2016 |

OTHER PUBLICATIONS

Extended European Search Report issued in European Application No. 17169678.4 dated Sep. 18, 2017.

(Continued)

*Primary Examiner* — Nicholas J Plionis
(74) *Attorney, Agent, or Firm* — Lerner, David, Littenberg, Krumholz & Mentlik, LLP

(57) ABSTRACT

A rotation shaft includes a body, a threaded rod, an anvil, a linkage, and a biasing member. The body includes a threaded portion disposed along an inner surface of a longitudinal throughhole. The threaded rod includes a distal end, the threaded rod configured to engage the threaded portion. The anvil is coupled to the distal end of the threaded rod. The linkage is coupled to the anvil. The biasing member is partially disposed about the linkage distal of the anvil, wherein rotation of the threaded rod translates into linear movement of the linkage relative to the body.

8 Claims, 8 Drawing Sheets

(56) References Cited

U.S. PATENT DOCUMENTS

| | | |
|---|---|---|
| 5,910,141 A | 6/1999 | Morrison et al. |
| 5,944,658 A | 8/1999 | Koros et al. |
| 5,951,564 A | 9/1999 | Schroder et al. |
| 6,123,707 A | 9/2000 | Wagner |
| 6,200,322 B1 | 3/2001 | Branch et al. |
| 6,416,521 B1 | 7/2002 | Waldner et al. |
| 6,440,133 B1 | 8/2002 | Beale et al. |
| 6,488,682 B2 | 12/2002 | Kikuchi et al. |
| 6,616,605 B2 | 9/2003 | Wright et al. |
| 6,648,888 B1 | 11/2003 | Shluzas |
| 6,660,006 B2 | 12/2003 | Markworth et al. |
| 6,743,231 B1 | 6/2004 | Gray et al. |
| 6,746,449 B2 | 6/2004 | Jones et al. |
| 6,790,208 B2 | 9/2004 | Oribe et al. |
| 6,790,209 B2 | 9/2004 | Beale et al. |
| 6,849,064 B2 | 2/2005 | Hamada |
| 6,923,814 B1 | 8/2005 | Hildebrand et al. |
| 6,929,606 B2 | 8/2005 | Ritland |
| 6,932,822 B2 | 8/2005 | Oribe et al. |
| 6,957,758 B2 | 10/2005 | Aranyi |
| 7,008,422 B2 | 3/2006 | Foley et al. |
| 7,011,660 B2 | 3/2006 | Sherman et al. |
| 7,083,621 B2 | 8/2006 | Shaolian et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,226,453 B2 | 6/2007 | Chao et al. |
| 7,250,052 B2 | 7/2007 | Landry et al. |
| 7,371,239 B2 | 5/2008 | Dec et al. |
| 7,462,182 B2 | 12/2008 | Lim |
| 7,473,267 B2 | 1/2009 | Nguyen et al. |
| 7,481,813 B1 | 1/2009 | Purcell |
| 7,491,207 B2 | 2/2009 | Keyer et al. |
| 7,491,208 B2 | 2/2009 | Pond, Jr. et al. |
| 7,497,869 B2 | 3/2009 | Justis |
| 7,520,879 B2 | 4/2009 | Justis et al. |
| 7,547,318 B2 | 6/2009 | Birkmeyer et al. |
| 7,563,264 B2 | 7/2009 | Landry et al. |
| 7,572,264 B2 | 8/2009 | Null et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,591,836 B2 | 9/2009 | Dick et al. |
| 7,608,081 B2 | 10/2009 | Abdelgany |
| 7,611,517 B2 | 11/2009 | Lim |
| 7,618,442 B2 | 11/2009 | Spitler et al. |
| 7,621,918 B2 | 11/2009 | Jackson |
| 7,625,379 B2 | 12/2009 | Puno et al. |
| 7,637,914 B2 | 12/2009 | Stern |
| 7,651,502 B2 | 1/2010 | Jackson |
| 7,655,008 B2 | 2/2010 | Lenke et al. |
| 7,666,189 B2 | 2/2010 | Gerber et al. |
| 7,691,132 B2 | 4/2010 | Landry et al. |
| 7,708,763 B2 | 5/2010 | Selover et al. |
| 7,776,040 B2 | 8/2010 | Markworth et al. |
| 7,854,751 B2 | 12/2010 | Sicvol et al. |
| 7,887,541 B2 | 2/2011 | Runco et al. |
| 7,909,835 B2 | 3/2011 | Oribe et al. |
| 7,922,749 B2 | 4/2011 | Dewey |
| 7,927,334 B2 | 4/2011 | Miller et al. |
| 7,946,982 B2 | 5/2011 | Hamada |
| 7,955,355 B2 | 6/2011 | Chin |
| 7,988,694 B2 | 8/2011 | Barrus et al. |
| 8,002,798 B2 | 8/2011 | Chin et al. |
| 8,147,524 B2 | 4/2012 | Piza Vallespir |
| 8,192,438 B2 | 6/2012 | Garamszegi |
| 8,230,863 B2 | 7/2012 | Ravikumar et al. |
| 8,298,138 B2 | 10/2012 | Gorek et al. |
| 8,303,595 B2 | 11/2012 | Jones |
| 8,308,729 B2 | 11/2012 | Nunley et al. |
| 8,308,774 B2 | 11/2012 | Hoffman et al. |
| 8,956,360 B2 | 2/2015 | Boachie-Adjei et al. |
| 8,961,523 B2 | 2/2015 | Barrus et al. |
| 9,198,698 B1 | 12/2015 | Doose et al. |
| 9,452,000 B2 | 9/2016 | Barrus |
| 9,943,344 B2* | 4/2018 | Mladenov ........... A61B 17/7002 |
| 2002/0052603 A1 | 5/2002 | Nichols et al. |
| 2003/0225408 A1 | 12/2003 | Nichols et al. |
| 2004/0147937 A1 | 7/2004 | Dunbar et al. |
| 2004/0215190 A1 | 10/2004 | Nguyen et al. |
| 2004/0230191 A1 | 11/2004 | Frey et al. |
| 2004/0267275 A1 | 12/2004 | Cournoyer et al. |
| 2005/0059969 A1 | 3/2005 | McKinley |
| 2005/0143749 A1 | 6/2005 | Zalenski et al. |
| 2005/0149053 A1 | 7/2005 | Varieur et al. |
| 2005/0192587 A1 | 9/2005 | Lim |
| 2005/0192589 A1 | 9/2005 | Raymond et al. |
| 2005/0261702 A1 | 11/2005 | Oribe et al. |
| 2005/0277934 A1 | 12/2005 | Vardiman |
| 2006/0025769 A1 | 2/2006 | Dick et al. |
| 2006/0036254 A1 | 2/2006 | Lim |
| 2006/0036260 A1 | 2/2006 | Runco et al. |
| 2006/0074418 A1 | 4/2006 | Jackson |
| 2006/0089651 A1 | 4/2006 | Trudeau et al. |
| 2006/0200132 A1 | 9/2006 | Chao et al. |
| 2006/0253120 A1* | 11/2006 | Anderson ............ A61B 17/808 606/86 R |
| 2006/0271050 A1 | 11/2006 | Piza Vallespir |
| 2007/0016193 A1 | 1/2007 | Ritland |
| 2007/0055247 A1 | 3/2007 | Jahng |
| 2007/0093817 A1 | 4/2007 | Barrus et al. |
| 2007/0213716 A1 | 9/2007 | Lenke et al. |
| 2007/0213722 A1 | 9/2007 | Jones et al. |
| 2007/0260261 A1 | 11/2007 | Runco et al. |
| 2007/0270811 A1 | 11/2007 | Dewey |
| 2007/0270867 A1 | 11/2007 | Miller et al. |
| 2007/0276379 A1 | 11/2007 | Miller et al. |
| 2007/0282337 A1 | 12/2007 | Garamszegi |
| 2008/0015601 A1 | 1/2008 | Castro et al. |
| 2008/0172062 A1* | 7/2008 | Donahue ............ A61B 17/7037 606/104 |
| 2009/0018593 A1 | 1/2009 | Barrus et al. |
| 2009/0143828 A1 | 6/2009 | Stad et al. |
| 2009/0228053 A1* | 9/2009 | Kolb ................. A61B 17/7076 606/86 A |
| 2009/0281579 A1* | 11/2009 | Weaver ................ A61B 17/025 606/286 |
| 2010/0121385 A1 | 5/2010 | Blain et al. |
| 2011/0054259 A1 | 3/2011 | Gorek et al. |
| 2011/0118791 A1 | 5/2011 | Nunley et al. |
| 2011/0172714 A1 | 7/2011 | Boachie-Adjei et al. |
| 2011/0257692 A1 | 10/2011 | Sandstrom et al. |
| 2012/0083853 A1 | 4/2012 | Boachie-Adjei et al. |
| 2012/0191144 A1 | 7/2012 | Peultier et al. |
| 2012/0271365 A1 | 10/2012 | Daubs et al. |
| 2012/0277808 A1 | 11/2012 | May |
| 2013/0018419 A1* | 1/2013 | Rezach ............. A61B 17/7076 606/264 |
| 2013/0041228 A1 | 2/2013 | Gorek et al. |
| 2013/0046344 A1 | 2/2013 | Nunley et al. |
| 2013/0245702 A1 | 9/2013 | McBride |
| 2013/0345759 A1* | 12/2013 | Meyer ................ A61B 17/7074 606/279 |
| 2014/0163617 A1 | 6/2014 | Boachie-Adjei et al. |
| 2014/0163625 A1* | 6/2014 | Meyer .............. A61B 17/7086 606/86 A |
| 2014/0277170 A1* | 9/2014 | Barrett .............. A61B 17/708 606/279 |
| 2015/0066042 A1 | 3/2015 | Cummins et al. |
| 2015/0100097 A1 | 4/2015 | Barrus |
| 2015/0100098 A1 | 4/2015 | Moore |
| 2015/0272628 A1 | 10/2015 | Kishan et al. |
| 2016/0206354 A1 | 7/2016 | Mladenov et al. |
| 2017/0325855 A1* | 11/2017 | Roger ................ A61B 17/7086 |

OTHER PUBLICATIONS

Communication for Application No. EP 17169678.4 dated Oct. 18, 2019, 2 pages.

* cited by examiner

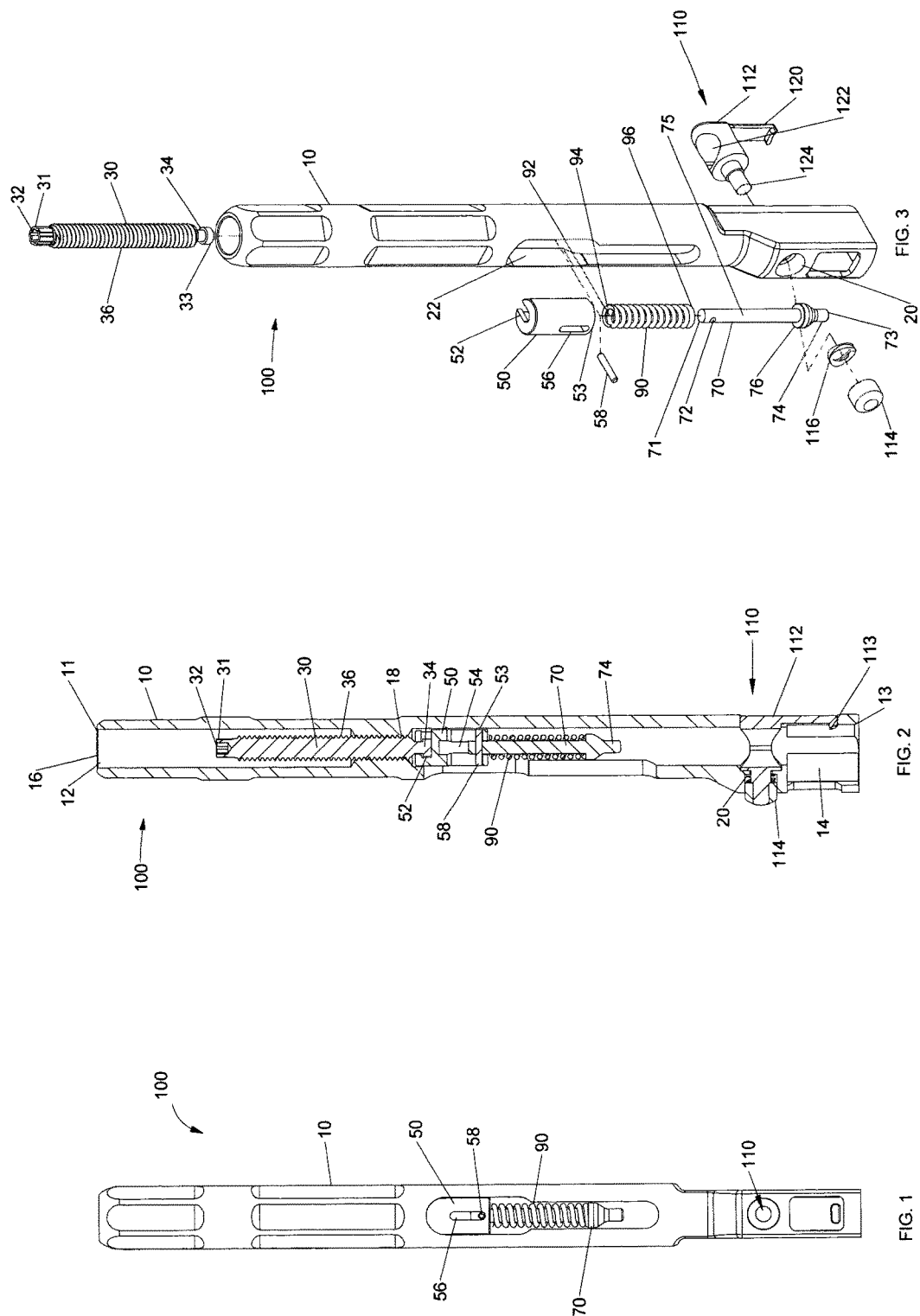

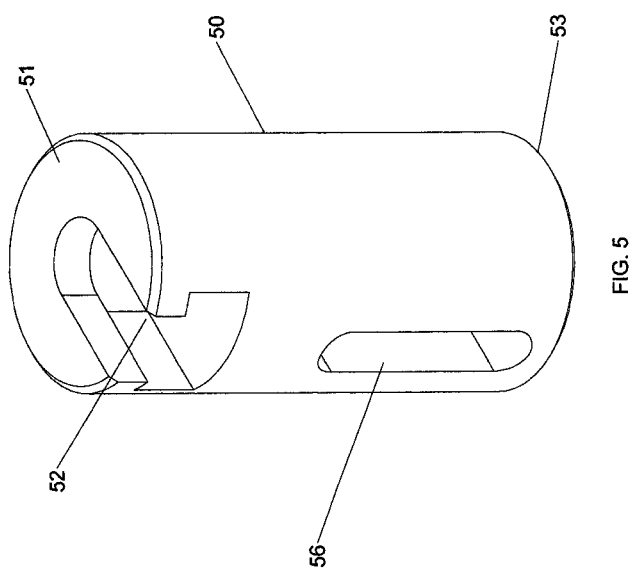

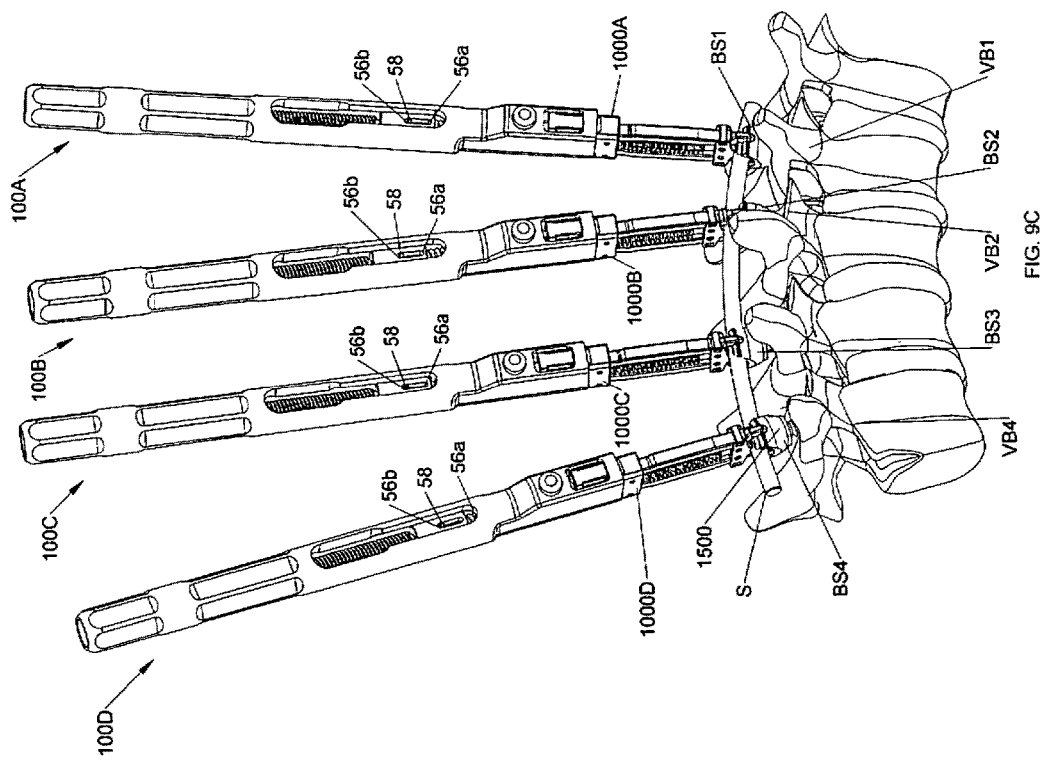

ROTATION SHAFT FOR A ROD REDUCER

CROSS-REFERENCE TO RELATED APPLICATIONS

This application claims priority to, and the benefit of, U.S. Provisional Patent Application Ser. No. 62/332,679, filed May 6, 2016, the entire contents of which are hereby incorporated by reference.

BACKGROUND

Technical Field

The present disclosure relates to orthopedic surgery apparatus for stabilizing and fixing the bones and joints of the body. Particularly, the present disclosure relates to a rotation shaft for a rod reducer.

Description of Related Art

The spinal column is a complex system of bones and connective tissues that provide support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending, and rotational loads and motions.

There are various disorders, diseases, and types of injury that the spinal column may experience in a lifetime. The problems may include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above-mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part or the entire intervertebral disc to form a rigid column of bone, which is stabilized by mechanical hardware.

The mechanical hardware used to immobilize the spinal column typically involves a series of bone screws or anchors, and metal rods or plates. When the spine surgery is performed posteriorly, it is common practice to place bone screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of one or more bone screws, followed by securing the spinal rod therein, may cause the clinician to use a number of instruments and expend a great deal of time and effort. The repeated process of inserting and securing the spinal rod into one or more bone screws secured to adjacent vertebrae can be difficult, tiresome, and time consuming. Further, alignment of the spinal rod as it's connected between sequential bone screws may require adjustment, and therefore, it is desirable that an apparatus and method be provided by which the spinal rod can be reduced into the screw housing of each of the sequentially aligned bone screws and, as necessary, provide for adjustment so as to facilitate the process for the clinician with minimal effort and loss of time. Therefore, a need exits for an efficient way to reduce the spinal rod into the screw housing and lock the spinal rod in place.

SUMMARY

The present disclosure is directed to a rotation shaft including a body, a threaded portion, an anvil, a linkage, and a biasing member. The body includes a threaded portion disposed along an inner surface of a longitudinal throughhole. The threaded rod includes a distal end and is configured to engage the threaded portion. The anvil is coupled to the distal end of the threaded rod. The linkage is coupled to the anvil. The biasing member is partially disposed about the linkage and distal of the anvil. Rotation of the threaded rod translates into linear movement of the linkage relative to the body.

In another embodiment, the rotation shaft may further include a button assembly disposed within a receiving cavity of the body. The button assembly includes a latch, a button, and a biasing element. The latch includes a hooked portion, an elongated throughhole, and a post. The button is disposed about the post and is configured to transition the latch between an engaged configuration and a disengaged configuration. The biasing element is disposed about the post and is configured to bias the button towards one of the engaged or disengaged configurations. In a further embodiment, the hooked portion of the latch may be configured to engage a recess of a rod reducer with the button assembly in the engaged configuration, such that longitudinal translation of the body with respect to the rod reducer is thereby inhibited.

In an embodiment, the linkage may further include an engagement portion configured to mechanically engage a head of a shaft of a rod reducer such that linear translation is communicated therebetween.

In a further embodiment, the threaded rod may define a key feature at the distal end thereof, and the anvil defines a key recess at a first end thereof. The key feature is configured to engage the key recess such that the threaded rod and the anvil are releasably couplable.

In yet another embodiment, the biasing member may be a compression spring.

In another aspect of the present disclosure, a system for reducing a spinal rod includes a rotation shaft and a rod reducer. The rotation shaft is configured to couple with the rod reducer and includes a body, a rod, an anvil, a linkage, and a biasing member. The body includes a threaded portion disposed along an inner surface of a longitudinal throughhole. The threaded rod includes a distal end and threads configured to engage the threaded portion. The anvil is coupled to the distal end of the threaded rod. The linkage is coupled to the anvil. The biasing member is partially disposed about the linkage and distal of the anvil. Rotation of the threaded rod translates into linear movement of the linkage relative to the body. The rod reducer is configured to couple with a bone screw and reduce a spinal rod therein. The rod reducer includes a housing, an anvil, a first arm member, and a second arm member. The housing has a shaft slidably disposed therethrough. The shaft defines a head at a proximal end thereof configured to engage the linkage of the rotation shaft. The anvil is coupled to a distal end of the shaft, and is configured to engage a spinal rod. The first and second arm members are operably coupled to the anvil and the housing and are transitionable between a first orientation, coupled with a bone screw, and a second orientation, uncoupled from a bone screw. Proximal and distal translation of the shaft, with respect to the housing, transitions the first and second arm members between the first and second orientations.

In an embodiment, the rotation shaft may further include a button assembly configured to selectively fix the rod reducer thereto. The button assembly is disposed within a receiving cavity of the body and includes a latch, a button, and a biasing element. The latch includes a hooked portion, an elongated throughhole, and a post. The button is disposed about the post and is configured to transition the latch between an engaged configuration and a disengaged configuration. The biasing element is disposed about the post and is configured to bias the button into one of the engaged or disengaged configurations. In a further embodiment, the hooked portion of the latch may be configured to engage a recess of the rod reducer with the button assembly in the engaged configuration, such that longitudinal translation of the body with respect to the rod reducer is thereby inhibited.

In a further embodiment, the system may further include a plurality of rotation shafts and a plurality of rod reducers.

In another aspect of the present disclosure, a method for reducing a spinal rod includes, coupling a first rod reducer to a first bone screw, positioning a spinal rod between an anvil of the first rod reducer and a screw housing of the first bone screw, and coupling a first rotation shaft to the first rod reducer such that a linkage of the first rotation shaft is coupled to a shaft of the first rod reducer. The method also includes rotating a threaded rod of the first rotation shaft such that the linkage translates distally with respect to a body of the first rotation shaft. The linkage drives the shaft of the first rod reducer distally with respect to a housing of the first rod reducer, such that the anvil of the first rod reducer is brought into contact with an outer surface of the spinal rod. The method further includes biasing the linkage, the shaft of the first rod reducer, and the anvil of the first rod reducer distally, via a biasing member partially disposed about the linkage, against the outer surface of the spinal rod. The method also includes translating the anvil of the first rod reducer distally via rotation of the threaded rod of the first rotation shaft.

In an embodiment, the method may further include absorbing and dampening a force exerted proximally by the spinal rod against the anvil of the first rod reducer.

In another embodiment, the method may further include maintaining abutment between the anvil of the first rod reducer and the outer surface of the spinal rod via the distal bias of the biasing member.

In yet another embodiment, the method may further include rotating the threaded rod of the first rotation shaft such that the threaded rod translates proximally with respect to the body of the first rotation shaft, and decoupling the first rod reducer from the first bone screw.

In a further embodiment, the method may further include coupling a second rod reducer to a second bone screw, positioning the spinal rod between an anvil of the second rod reducer and a screw housing of the second bone screw, and coupling a second rotation shaft to the second rod reducer such that a linkage of the second rotation shaft is coupled to a shaft of the second rod reducer. The method also includes rotating a threaded rod of the second rotation shaft such that the linkage translates distally with respect to a body of the second rotation shaft. The linkage drives the shaft of the second rod reducer distally with respect to a housing of the second rod reducer, such that the anvil of the second rod reducer is brought into contact with an outer surface of the spinal rod. The method also includes biasing the linkage, the shaft of the second rod reducer, and the anvil of the second rod reducer distally, via a biasing member partially disposed about the linkage, against the outer surface of the spinal rod. Further still, the method includes translating the anvil of the second rod reducer distally via rotation of the threaded rod of the second rotation shaft.

In another embodiment, the method may further include maintaining abutment between the anvil of the second rod reducer and the outer surface of the spinal rod, via the distal bias of the biasing member of the second rotation shaft, during the distal translation of the anvil of the first rod reducer.

BRIEF DESCRIPTION OF THE DRAWINGS

The above and other aspects and features of the present disclosure will become more apparent in light of the following detailed description when taken in conjunction with the accompanying drawings in which:

FIG. 1 is a side view of a rotation shaft in accordance with the present disclosure;

FIG. 2 is a side cross-sectional view of the rotation shaft of FIG. 1;

FIG. 3 is a perspective view, with parts separated, of the rotation shaft of FIG. 1;

FIG. 5 is a perspective view of an anvil of the rotation shaft of FIG. 1;

FIG. 9C is a perspective view of the construct of FIG. 8A with the spinal rod completely reduced.

DETAILED DESCRIPTION OF EMBODIMENTS

Figure 4:
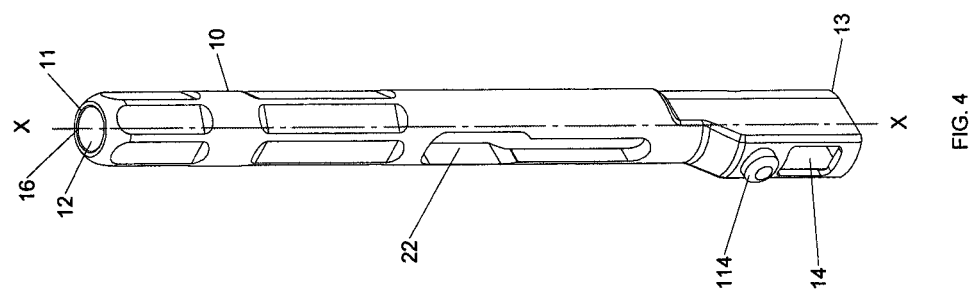
FIG. 4 is a perspective view of a body of the rotation shaft of FIG. 1.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the component thereof that is closer to the clinician and the term "distal" will refer to the portion of the or component thereof that is farther from the clinician. Additionally, in the drawings and in the description that follows, terms such as front, rear, upper, lower, top, bottom, and similar directional terms are used simply for convenience of description and are not intended to limit the disclosure.

Referring initially to FIGS. 1-5, a rotation shaft in accordance with the present disclosure is generally designated as rotation shaft 100. Rotation shaft 100 includes a body 10, a threaded rod 30, an anvil 50, a linkage 70, and a biasing member 90. Rotation shaft 100 may further include a button assembly 110 configured to selectively engage and disengage a rod reducer 1000, as discussed below. Body 10 is configured to house threaded rod 30, anvil 50, linkage 70, biasing member 90, and button assembly 110 therein. Generally, threaded rod 30 may be releasably coupled to anvil 50, and anvil 50 may be releasably coupled to linkage 70 and biasing member 90, where biasing member 90 is distal of anvil 50. More particularly, biasing member 90 surrounds a portion of linkage 70 and is disposed between anvil 50 and an engagement portion 74 of linkage 70. With brief reference to FIGS. 9A-9C, rotation shaft 100 may be coupled with rod reducer 1000 such that rotation shaft 100 and rod reducer 1000 cooperatively act to reduce a spinal rod S into one or more bone screws BS1-BSn implanted sequentially into adjacent vertebral bodies VB1-VBn, as discussed below.

Body 10 defines an opening 12 at a first end 11, a receiving cavity 14 proximate a second end 13, and a longitudinal throughhole 16 therebetween. Further, a portion of throughhole 16 includes a threaded portion 18 (FIG. 2) thereon configured to engage threaded rod 30. Further still, body 10 defines a button hole 20 in communication with receiving cavity 14 that is configured to receive a button 114 of button assembly 110, as discussed below. Receiving cavity 14 is configured to receive a portion of rod reducer 1000, such that rotation shaft 100 and rod reducer 1000 may be selectively coupled.

Threaded rod 30 includes a drive head 32 proximate a proximal end 31, a key feature 34 proximal a distal end 33, and threads 36 therebetween. Threaded rod 30 is disposed within throughhole 16 of body 10, where threads 36 cooperatively engage threaded portion 18. Threaded rod 30 is configured to translate linearly relative to body 10 via the threaded engagement of threads 36 and threaded portion 18. It is envisioned that drive head 32 may be configured to cooperatively engage with any number of counterpart drive tools known in the art to effect torque driven rotation. For example, drive head 32 may be configured to receive a hex head (as shown in FIG. 3) or a Philips or slotted screwdriver. Threads 36 and threaded portion 18 of threaded rod 30 and body 10, respectively, permit torque driven rotation and proximal and distal translation of the threaded rod 30 with respect to body 10. More particularly, threaded rod 30 is rotatable about a longitudinal axis X (FIG. 4) of body 10 such that rotation of threaded rod 30 in a first direction (e.g., clockwise) corresponds to translation thereof in a first direction (e.g., distally), and rotation of threaded rod 30 in a second, opposite direction (e.g., counter-clockwise) corresponds to translation thereof in a second, opposite direction (e.g., proximally).

Anvil 50 includes a key recess 52 proximate a first end 51 configured to receive the key feature 34 of threaded rod 30, such that linear translation of threaded rod 30, as discussed above, corresponds to linear translation of anvil 50. Anvil 50 defines a cavity 54 proximate a second end 53 (FIG. 2) and in communication with a slot 56, such that a pin 58 is slidable therein. It should be appreciated that key recess 52 and key feature 34, and pin 58 and slot 56, cooperatively act to facilitate the selective assembly of threaded rod 30 and anvil 50, and anvil 50 and linkage 70, respectively. Further, the position of pin 58 with respect to slot 56 provides visual indicia of the compression of biasing member 90, as discussed below.

Figure 7A:
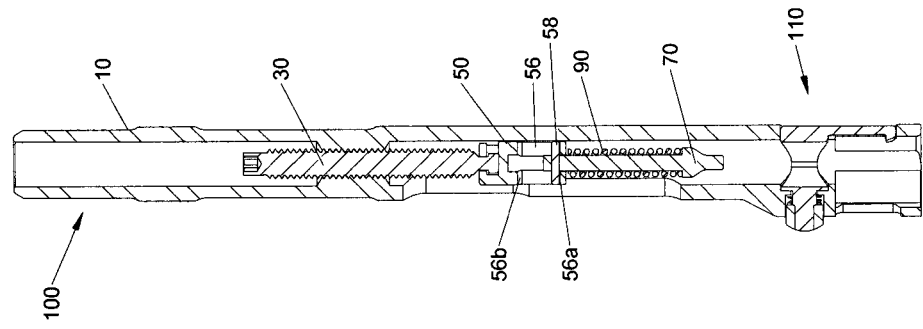
FIG. 7A is a perspective view of the rotation shaft of FIG. 1 in a compressed configuration.
Figure 7B:
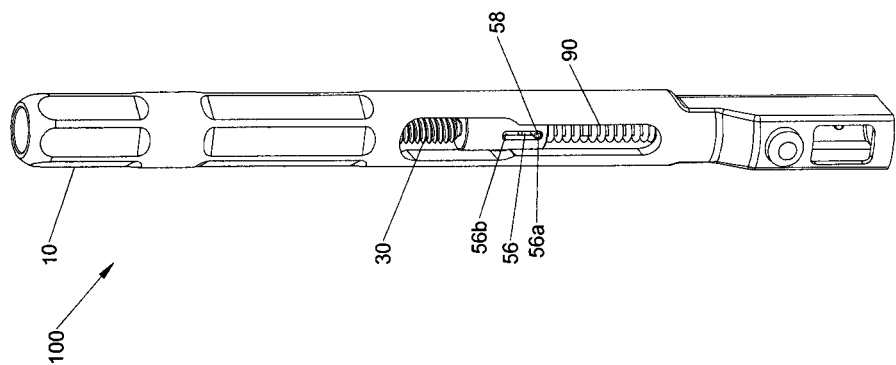
FIG. 7B is a side cross-sectional view of the rotation shaft of FIG. 7A.

Linkage 70 includes a pinhole 72 proximate a first end 71, the engagement portion 74 proximate a second end 73, and a shaft 75 extending therebetween. Linkage 70 is coupled to anvil 50, via pin 58, pinhole 72, and slot 56, where biasing member 90 is positioned between the second end 53 of anvil 50 and engagement portion 74. More particularly, shaft 75 is configured to be received within a lumen 92 of biasing member 90, where a first end 94 of biasing member 90 is positioned proximate the second end 53 of anvil 50 and a second end 96 of biasing member 90 is positioned proximal of second end 73 and in abutment with a flange 76 of linkage 70. Biasing member 90 may be configured to bias linkage 70 in either a first direction (e.g., distally and away from anvil 50) or in a second direction (e.g., proximally and towards anvil 50). Accordingly, biasing member 90 biases anvil 50 away from, or towards, engagement portion 74 and towards, or away from, first end 71 of linkage 70, respectively. It should be appreciated that as the bias provided by biasing member 90 is overcome, and linkage 70 translates either proximally or distally with respect to anvil 50, pin 58 slides proximally or distally within slot 56, as illustrated in FIGS. 7A and 7B. Engagement portion 74 of linkage 70 is configured to engage a head of a shaft 1110 of rod reducer 1000, such that linear translation of linkage 70, with respect to body 10, directs linear translation of shaft 1110, as discussed below. Body 10 may further include a window 22 defined therein, such that anvil 50, linkage 90, and the position of pin 58 within slot 56 may be easily visible during reduction of spinal rod S.

Figure 8B:
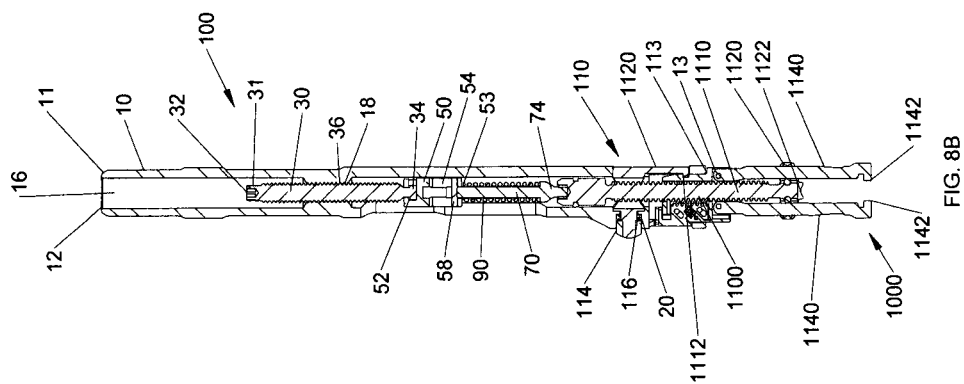
FIG. 8B is a side cross-sectional view of the rotation shaft and rod reducer of FIG. 8A.
Figure 8A:
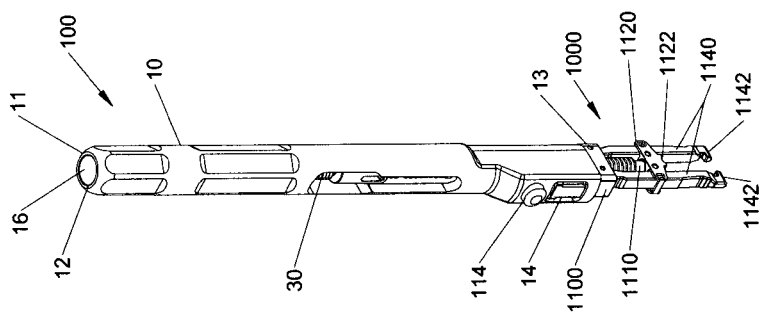
FIG. 8A is a side perspective view of the rotation shaft of FIG. 1 coupled to a rod reducer.

Button assembly 110 includes a latch 112 in communication with receiving cavity 14, button 114, and a biasing element 116 wherein button 114 and biasing element 116 are disposed in button hole 20. Latch 112 includes a hooked portion 120, an elongated throughhole 122, and a post 124, wherein post 124 extends into button hole 20. Biasing element 116 and button 114 are disposed on post 124, where button 114 is coupled post 124 via frictional engagement, chemical bonding, threaded engagement, or any means known in the art to secure button 114 thereto. Elongated throughhole 112 is configured to align with the longitudinal axis X of body 10, such that linkage 70 may translate therethrough. It is envisioned that elongated throughhole 112 permits linkage 70 to pass therethrough with button assembly 110 in either an engaged or disengaged configuration. More particularly, button assembly 110 selectively engages and disengages with a portion of rod reducer 1000, such that rotation shaft 100 and rod reducer 1000 may be selectively coupled and uncoupled. Button 114 transitions latch 112, and thus button assembly 110, between the engaged configuration, wherein latch 112 engages a portion of rod reducer 1000, and the disengaged configuration, where latch 112 is spaced away from rod reducer 1000. It is envisioned that latch 112 may be rigid, such that latch 112 may slide transversely with respect to longitudinal axis X into and out of engagement with rod reducer 1000. Alternatively, latch 112 may be flexible, such that hooked portion 120 may flex into and out of engagement with rod reducer 1000. Biasing element 116 may be configured to bias button 114, and thus button assembly 110, into one of the engaged or disengaged configurations, such that rotation shaft 100 may be biased to either engage or disengage rod reducer 1000. Accordingly, once a portion of rod reducer 1000 is inserted into receiving cavity 14 of rotation shaft 100, the bias of button 114 brings latch 120 into engagement with rod reducer 1000, thus fixably coupling rotation shaft 100 and rod reducer 1000. Further still, hooked portion 120 may be configured to engage a corresponding recess 1112 (FIG. 8B) of rod reducer 1000 in the engaged configuration, such that linear translation of rod reducer 1000, with respect to rotation shaft 100, is further inhibited.

Briefly, rod reducer 1000 is configured to grasp a screw housing 1500 of a bone screw BS and to control reduction of spinal rod S (FIGS. 8A-9C) into a rod receiving recess defined within the screw housing 1500 of the bone screw BS. In particular, rod reducer 1000 includes a housing 1100 receivable within receiving cavity 14 of rotation shaft 100, a shaft 1110 including a head at a proximal end thereof and an anvil 1120 at a distal end thereof, and a pair of arm members 1140 operably coupled to anvil 1120 and housing 1100. During reduction of spinal rod S, anvil 1120 is configured to abut and drive a portion of spinal rod S into proximity with screw housing 1500. Housing 1100 further includes recess 1112 configured to selectively receive hooked portion 120 of latch 112 with button assembly 110 in the engaged configuration, such that linear translation of rod reducer 1000 with respect to rotation shaft 100 is inhibited.

Engagement portion 74 of linkage 70 operably engages the head of shaft 1110 to facilitate remote operation thereof, such that rotation shaft 100 and rod reducer 1000 form an associated structure and cooperatively act to reduce spinal rod S. Thus, rotation of threaded rod 30 via a drive tool (not shown) drives anvil 50 and linkage 70 coupled thereto linearly, with respect to body 10, which further drives shaft 1110 coupled with linkage 70 linearly, with respect to housing 1100 of rod reducer 1000. Accordingly, proximal and distal translation of linkage 70 corresponds to proximal and distal translation of shaft 1110, and vice versa.

As a result of proximal and distal translation of shaft 1110, with respect to housing 1100, anvil 1120 translates proximally and distally with respect to housing 1110 and arm members 1140 pivot or flex into and out of engagement with screw housing 1500. More particularly, translation of shaft 1110 in a first direction (e.g., distally) translates anvil 1120 in a first direction (e.g., distally) and pivots or flexes arm members 1140 into a first orientation (e.g., towards one another and into a parallel configuration) such that a hooked portion 1142 of each arm member 1140 grasps screw housing 1500. Translation of shaft 1110 in a second, opposite direction (e.g., proximally) translates anvil 1120 in a second, opposite direction (e.g., proximally) and pivots or flexes arm members 1140 into a second orientation (e.g., away from one another and into a spaced apart configuration) such that hooked portion 1142 of each arm member 1140 uncouples from screw housing 1500. Engagement of hook portion 1142 to bone screw BS serves to maintain alignment of rod reducer 1000 with respect to the screw housing 1500 as spinal rod S is reduced therein. With arm members 1140 in the first orientation, rod reducer 1000 and bone screw BS are coupled, and with arm members 1140 in the second configuration rod reducer 1000 may be selectively engaged or disengaged from bone screw BS.

Further discussion regarding rotation shaft 100, rod reducer 1000, and related medical devices may be found in commonly owned U.S. Pat. No. 8,961,523, filed Jul. 13, 2007 and entitled "Rod Reduction Devices and Method of Use"; U.S. Pat. No. 8,308,729, filed Dec. 9, 2010 and entitled "Rod Reduction Device"; U.S. Pat. No. 8,956,360, filed Oct. 3, 2011 and entitled "Devices, Systems, and Methods For Performing Spinal Surgery"; U.S. Patent Application Publication No. 2015/0100097, filed Oct. 7, 2014 and entitled "Rod Reducer"; U.S. Patent Application Publication No. 2015/0100098, filed Oct. 7, 2014 and entitled "Rod Reducer"; U.S. Patent Application Publication No. 2015/0272628, filed Apr. 1, 2015 and entitled "Spinal Fixation Device"; PCT/US2015/053386 filed Oct. 1, 2015 and entitled "Rod Reducer"; and U.S. patent application Ser. No. 14/996,368, filed Jan. 15, 2016 and entitled "Rod Reducer", the contents of each of which are hereby incorporated by reference herein in their entirety.

Figure 9A:
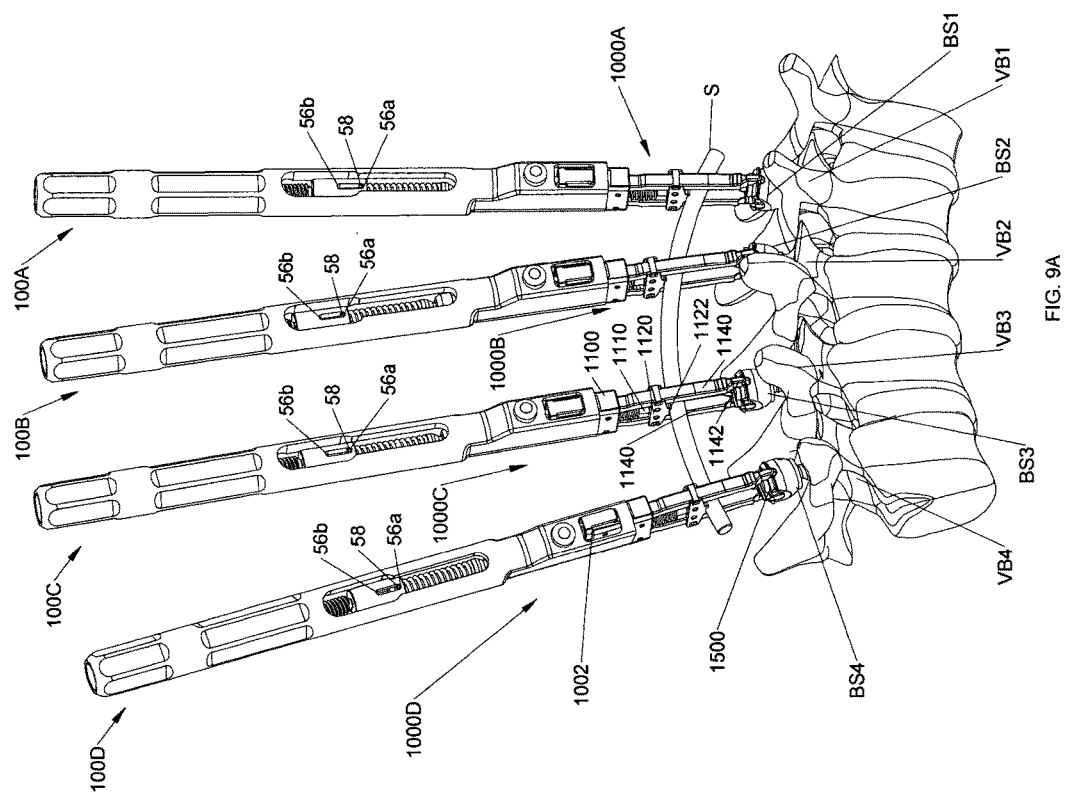
FIG. 9A is a perspective of a screw construct including a plurality of rotation shafts of FIG. 1 coupled to a plurality of rod reducers and pedicle screws with a spinal rod coupled to the plurality of rod reducers.
Figure 9B:
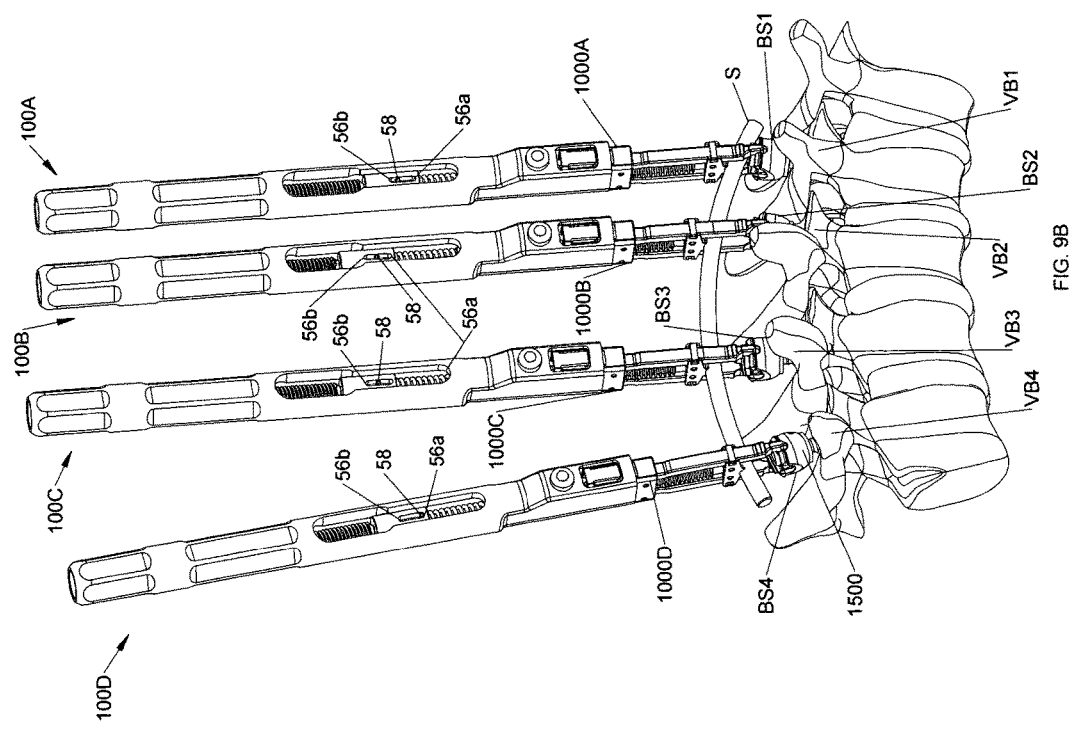
FIG. 9B is a perspective view of the construct of FIG. 8A with the spinal rod partially reduced.

During reduction of spinal rod S, biasing member 90 disposed between anvil 50 and linkage 70 provides a biasing force therebetween, such that linkage 70, and thus anvil 1120 of rod reducer 1000 coupled thereto, is biased either away from, or towards, anvil 50. Biasing member 90 may represent, for example, a compression spring, an extension spring, or any biasing element known in the art. In one embodiment, biasing member 90 imparts or applies a distal biasing force on linkage 70, with respect to anvil 50, which is thus transmitted to anvil 1120, thereby biasing anvil 1120 distally towards bone screw BS. Biasing member 90 may pre-load the anvil 1120, thus providing a distally directed force upon the anvil 1120 and spinal rod S during reduction of spinal rod S. Biasing member 90 may provide a pre-load force between an approximate range of 1-50 pounds-force (lbf), and more preferably between 1-30 lbf. It is contemplated that the pre-load force may also have values between 1-75 lbf or 1-60 lbf or 1-40 lbf. Biasing member 90 further acts as a dampener during reduction of spinal rod S, such that a more uniform and constant force is applied thereto via anvil 1120 for a smooth reduction. As discussed below, it is envisioned that during an incremental reduction of spinal rod S between multiple bone screws BS fixed sequentially to adjacent vertebra, biasing member 90 acts as a dampener to facilitate the reduction of spinal rod S therein (FIGS. 9A-9C). More particularly, biasing member 90 serves to bias anvil 1120 distally against spinal rod S, and further, acts to absorb and dampen any resistive forces exerted proximally against anvil 1120 by spinal rod S during reduction and/or manipulation of spinal rod S.

With reference to FIGS. 6A-9C, during reduction of spinal rod S, a receiving saddle 1122 of anvil 1120 is in abutment with an outer surface of spinal rod S. It is envisioned that receiving saddle 1122 is configured to accommodate a range of spinal rod diameters. For example, receiving saddle 1122 may be configured to cooperatively engage a spinal rod S having a variance in diameter of approximate 3 mm to 8 mm, while still achieving the necessary driving force to secure the spinal rod S into bone screw BS. Receiving saddle 1122 may be generally arched or convex, but may take the form of any geometric shape adapted to cooperatively engage with and drive a spinal rod during reduction.

Figure 6A:
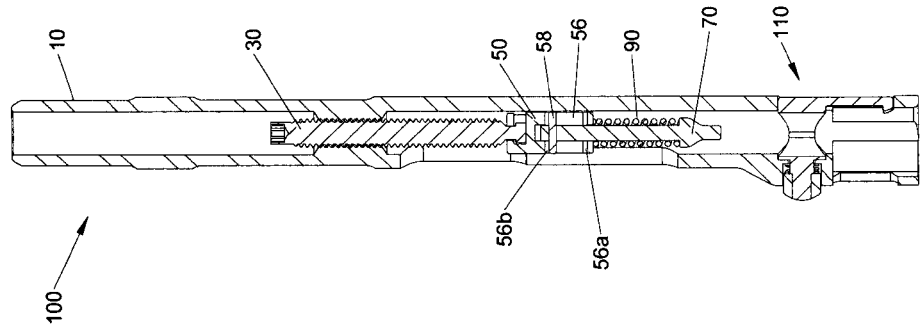
FIG. 6A is a perspective view of the rotation shaft of FIG. 1 in an uncompressed configuration.
Figure 6B:
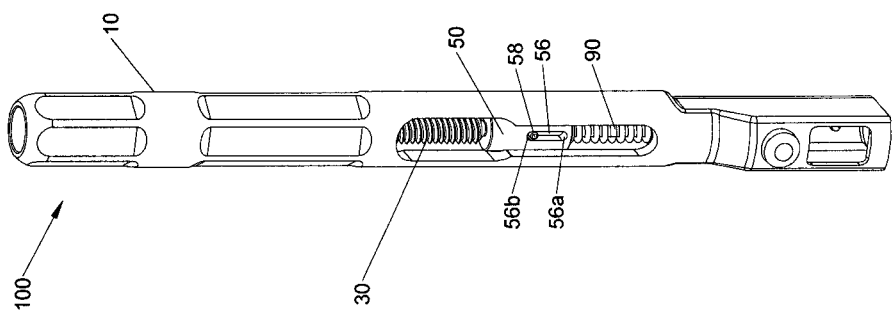
FIG. 6B is a side cross-sectional view of the rotation shaft of FIG. 6A.

During reduction of spinal rod S, and proximal and distal translation of anvil 50, linkage 70, and biasing member 90, biasing member 90 applies a proximal or distal bias to linkage 70 and thus anvil 1120, thereby causing anvil 1120 to also have a corresponding proximal or distal bias (i.e., towards or away from the rod receiving recess of bone screw BS; see FIGS. 9A-9C). In one embodiment, biasing member 90 biases linkage 70 distally and thus anvil 1120 distally, such that opposite and resistant forces exerted proximally against anvil 1120 are thereby dampened. More particularly, as anvil 50, linkage 70, and anvil 1120 translate distally, proximal resistance encountered by anvil 1120 is absorbed and dampened by the distally biased biasing member 90. As anvil 1120 encounters additional proximal resistance, such that the distal bias of biasing member 90 is overcome, pin 58 slides proximally within slot 56. The resulting resistance (i.e., a proximal load against anvil 1120) acts to compress biasing member 90, thus driving pin 58 proximally from a first end 56a of slot 56 (an uncompressed configuration, as illustrated in FIGS. 6A, 6B, and 9A) towards a second end 56b of slot 56 (a compressed configuration, as illustrated in FIGS. 7A, 7B, and 9C). As should be appreciated, anvil 1120 may encounter proximal resistance and loading as a result of the contact between anvil 1120 and spinal rod S during reduction thereof. Further, the distal bias provided by biasing member 90 acts to maintain contact between anvil 1120 and spinal rod S, and further ease the reduction of spinal rod S within screw housing 1500 by better distributing the load applied by anvil 1120 against spinal rod S and minimize point loading amongst the plurality of rotation shafts 100A-D.

Operating a rotation shaft in accordance with the present disclosure will be described with reference to FIGS. 1-9C. Generally, a spinal rod and screw construct is assembled in a patient as follows. A clinician implants bone screw BS into a spinal vertebra VB with screw housings 1500 of the bone screw BS positioned to receive a portion of spinal rod S in the receiving recess. It is envisioned that a clinician may implant multiple bone screw BS1-*n* sequentially into several adjacent spinal vertebra VB1-*n* during a procedure (FIGS. 9A-9C). Once the desired number of bone screws BS have been implanted, the clinician aligns and manipulates the spinal rod S such that a portion of the spinal rod S is in proximal relation to the screw housing 1500 of each respective bone screws BS, such that spinal rod S creates an unbroken connection between each bone screw BS.

The clinician next positions rod reducer 1000 into proximity with each respective bone screw BS, such that hook portion 1142 of arm members 1140 is in near abutment to the screw housing 1500 of each respective bone screw BS. Next, the clinician causes the hook portion 1142 to grasp, clip, or otherwise affix to the screw housing 1500, such that during reduction of spinal rod S attachment of the rod reducer 1000 to the bone screw BS, and alignment of spinal rod S to the screw housing 1500, is maintained. The clinician may insert a proximal end 1002 of rod reducer 1000 (FIGS. 8A and 8B) within receiving cavity 14 of rotation shaft 100 prior to fixing arm member 1140 to screw housing 1500, or thereafter, such that linkage 70 engages shaft 1110. Thereafter, threaded rod 30, anvil 50, linkage 70, and anvil 1120 are in cooperative engagement. Rod reducer 1000 and rotation shaft 100 may be selectively engaged or disengaged via button assembly 110. During reduction, spinal rod S is positioned between screw housing 1500, anvil 1120, and arm members 1140, and may be in abutment to anvil 1120 or in abutment to the screw housing 1500.

The clinician next reduces spinal rod S into screw housing 1500 via rotation of threaded rod 30 which caused distal translation of anvil 1120, as discussed above. Often times there may be 15 mm or more of travel required in order to reduce spinal rod S fully within screw housing 1500 such that spinal rod S and screw housing 1500 can be locked. Reduction of spinal rod S such a distance can be cumbersome, tedious, and time consuming. The distal bias to anvil 1120 provided by biasing member 90, via linkage 70, eases the reduction of spinal rod S. The load or force provided by biasing member 90 upon linkage 70, and thus anvil 1120 and spinal rod S, aids to maintain the position of, and connection between, anvil 1120 and spinal rod S. Biasing member 90 further acts to distribute the distal loading upon spinal rod S caused by anvil 1120, and minimizes point loading therebetween.

When utilizing multiple bone screws BS, multiple rotations shaft 100, and multiple rod reducers 1000, biasing member 90 of each respective rotation shaft 100 further serves to dampen any proximally directed forces exerted upon anvil 1120 of each respective rod reducer 1000 from spinal rod S. More particularly, with a plurality of rod reducers 1000, where each rod reducer 1000 is mounted to a different bone screw BS, the clinician is able to gradually or incrementally reduce the spinal rod S into each respective bone screws BS by sequentially reducing each rod reducer 1000 until all rod reducers 1000 have been fully reduced and spinal rod S is completely reduced into all of the adjacent bone screws BS. With rotation shaft 100 and rod reducer 1000 attached to bone screw BS, it is further envisioned that the clinician may use rotation shaft 100 and rod reducer 1000 to further assist the alignment of spinal rod S between multiple bone screws BS. The clinician is provided a mechanical advantage to further bend or shape spinal rod S while spinal rod S is securely held by both rod reducer 1000 and the screw housing 1500 of the bone screw BS. In this configuration, the clinician may make final adjustments to the spinal rod S when connecting spinal rod S between multiple bone screws BS. After spinal rod S is properly aligned, the clinician may further reduce spinal rod S to secure the spinal rod S into the screw housing 1500 of the bone screw BS.

With reference to FIGS. 8A-9C, a screw construct includes a plurality of bone screws BS1-BS4, a plurality of rotation shafts 100A-D, and a plurality of rod reducers 1000A-1000D. Initially, bone screws BS1-BS4 are implanted sequentially into adjacent vertebrae VB1-VB4. The surgeon can manipulate and correct the curve of the spinal column to a large degree prior to the reduction of spinal rod S. Further, the spinal rod S may be pre-bent to the configuration of the normal spinal curve, e.g., the sagittal curve. Once certain the spine is in the desired anatomical orientation, and/or spinal rod S is pre-bent, the surgeon can position spinal rod S relative to bone screws BS1-BS4 and rod reducers 1000A-1000D, and reduce spinal rod S into a first point of the spinal column, e.g., VB1, where the construct is to be attached. One or more rotation shafts 100A-100D may be coupled to rod reducers 1000A-1000D, as discussed above, where rod reducers 1000A-1000D may be sequentially operated, alternating from the ends toward the middle, from one end to the other, or any combination thereof depending upon the surgeon's technique to reduce spinal rod S into the screw housing 1500 of each respective bone screw BS1-BS4. It is noted that rod reducers 1000A-1000D may also be contemporaneously operated and need not be reduced sequentially.

It should be appreciated that as one or more rod reducers 1000A-1000D reduce spinal rod S, anvil 1120 of rod reducers 1000 actively reducing spinal rod S, and additionally anvil 1120 of rod reducers 1000 simply coupled to bone screws BS, may undergo resistance and/or encounter a proximally directed force from spinal rod S. Conversely, spinal rod S may move distally away from, and out of contact with, anvil 1120 as portions of spinal rod S are driven into proximity with a respective bone screw BS, such as, for example, during sequential reduction of spinal rod S. As spinal rod S moves out of contact with anvil 1120 of a respective rod reducer 1000, the attachment between rod reducer 1000 and bone screw BS may loosen or become completely decoupled. As should be appreciated, the abutment of anvil 1120 against spinal rod S provides axial stability between rod reducer 1000 and bone screw BS during reduction. As such, the distal bias of anvil 1120 caused by biasing member 90, via linkage 70 and shaft 1110, enhances the connection between anvil 1120 and spinal rod S, and thus enhances the coupling of rod reducer 1000 and bone screw BS. The distal bias and/or pre-load upon anvil 1120 created by biasing member 90 absorbs and dampens any proximal resistance exerted by spinal rod S against anvil 1120, and further maintains contact between anvil 1120 and spinal rod S thus increasing axial stability to enhance the attachment between rod reducer 1000 and bone screw BS.

As illustrated in FIGS. 8A-9C, each rotation shaft 100A-100D is coupled to a respective rod reducer 1000A-1000D, each rod reducer 1000A-1000D is coupled to a respective bone screw BS1-BS4 (i.e., the arms 1140 of each respective rod reducer 1000A-1000D are coupled to a respective bone screw BS1-BS4), each bone screw BS1-BS4 is coupled sequentially to adjacent vertebra bodies VB1-VB4, and spinal rod S is positioned between anvil 1120 of each respective rod reducer 1000A-1000D and screw housing 1500 of each respective bone screw BS1-BS4. As spinal rod S is sequential reduced via distal translation of anvil 1120 of one or more rod reducers 1000A-1000D, via distal translation of anvil 50 and linkage 70, portions of spinal rod S not being actively reduced may exert a force proximally, or alternatively, may move distally towards bone screws BS1-BS4. As a result, anvil 1120 may encounter a proximally directed force from spinal rod S, or conversely, may be caused to lose contact with spinal rod S, thus weakening the connection between rod reducer 1000 and bone screw BS.

For example, and as illustrated in FIG. 9A, spinal rod S may be sequentially reduced into four bone screws BS1-BS4 utilizing four rotation shafts 100A-100D and four rod reducers 1000A-1000D. Initially, anvil 1120 of each of rod reducer 1000A-1000D may be brought into contact with spinal rod S. Prior to reduction of spinal rod S, biasing member 90 of all of the rotation shafts 100A-100D is in the uncompressed configuration. As rod reducer 1000A begins to incrementally reduce spinal rod S, biasing member 90 of rotation shaft 100A coupled therewith, serves to distribute the load and minimize point loading caused by the distal driving force of anvil 1120 against spinal rod S. Further, as anvil 1120 of rod reducer 1000A drives spinal rod S distally, spinal rod S may move proximally against, or conversely move distally away from and out of contact with, the anvil 1120 of rod reducers 1000B-1000D. In such a situation, biasing member 90 is configured to absorb and dampen any proximally directed forces exerted upon anvil 1120 of rod reducers 1000B-1000D, and further, bias anvil 1120 distally to maintain contact between anvil 1120 and spinal rod S. Thus, biasing member 90 not only facilitates the reduction of rod reducer 1000A which is actively reducing spinal rod S, but further serves to stabilize rod reducers 1000B-1000D of the screw construct which are not actively being used to reduce spinal rod S. It should be appreciated that any of rod reducers 1000A-1000D may be used to actively reduce spinal rod S, where the biasing member 90 of the remaining rotation shafts 100A-D coupled to the remaining rod reducers 1000A-1000D serve to maintain the stability of the screw construct. Additionally, this maintains engagement between the rod reducers 1000A-1000D and their respective bone screws BS1-BS4.

As illustrated in FIG. 9B, all of the rod reducers 1000A-1000D are in a state of incremental reduction of spinal rod S, biasing members 90 of all of the rotation shafts 100A-100D are in a state of incremental compression between the compressed and uncompressed configurations, and spinal rod S is partially reduced. As illustrated in FIG. 9C, spinal rod S is fully reduced, anvils 1120 of each rod reducer 1000A-1000D are in the distal most position, and biasing members 90 of all of the rotation shafts 100A-100D are in the compressed configuration.

Upon final alignment of spinal rod S between one or more bone screws BS, and/or securement of spinal rod S into screw housing 1500 thereof, the clinician sequentially or contemporaneously rotates threaded shaft 30 of one or more rotation shafts 100 such that the respective anvil 50, linkage 70, and anvil 1120 coupled therewith translate proximally. As the clinician translates anvil 1120 towards a proximal most position, arm members 1140 of the respective rod reducer 1000 may be decoupled from the screw housing 1500, permitting the clinician to detach rod reducer 1000 from the respective bone screw BS. Rotation shaft 100 may be decoupled from rod reducer 1000, via button assembly 110, at any desired point during the procedure.

It is envisioned that the clinician may be provided with multiple spinal rods S. The clinician may perform the method described above to facilitate the reduction of multiple spinal rods S into multiple screw housings 1500 to a number of vertebrae in sequence. It is further envisioned that the clinician may be provided with multiple bone screws BS and spinal rods S of varying sizes.

In accordance with the present disclosure, a kit will be described with reference to FIGS. 1-9C. The kit includes rotation shaft 100 in a package (not shown). The kit may further include rod reducer 1000, bone screw BS, spinal rod S, an orthopedic tool or device (not shown), instructions for use, or any combination thereof. Examples of the orthopedic tool or device may be a tightening or loosening tool, an alignment tube, or a locking device. It is further envisioned, that the kit may include multiple rotation shafts 100, multiple rod reducers 1000, multiple bone screws BS, multiple spinal rods S, or any combination thereof. Further, the kit may include a variety of sizes of bone screws BS and spinal rods S. The package may include a thermoformed plastic tray and/or other packaging materials within the view of those skilled in the art, and may be further configured to withstand sterilization. Further still, rotation shaft 100, rod reducer 1000, bone screw BS, spinal rod S, an orthopedic tool or device, and a plurality or combination thereof, may be configured to withstand sterilization, either individually or in combination, with the package.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A rotation shaft comprising:
   a body including a threaded portion disposed along an inner surface of a longitudinal throughhole;
   a threaded rod including a distal end, the threaded rod configured to engage the threaded portion;
   an anvil coupled to the distal end of the threaded rod;
   a linkage coupled to the anvil
   a biasing member partially disposed about the linkage distal of the anvil, wherein rotation of the threaded rod translates into linear movement of the linkage relative to the body; and
   a button assembly disposed within a receiving cavity of the body, the button assembly including:

a latch including a hooked portion, an elongated throughhole, and a post; a button disposed about the post and configured to transition the latch between an engaged configuration and a disengaged configuration; and a biasing element disposed about the post and configured to bias the button towards one of the engaged or disengaged configurations.

2. The rotation shaft of claim 1, wherein the hooked portion of the latch is configured to engage a recess of a rod reducer with the button assembly in the engaged configuration, such that longitudinal translation of the body with respect to the rod reducer is thereby inhibited.

3. The rotation shaft of claim 1, wherein the threaded rod defines a key feature at the distal end thereof, and the anvil defines a key recess at a first end thereof, the key feature configured to engage the key recess such that the threaded rod and the anvil are releasably couplable.

4. The rotation shaft of claim 1, wherein the biasing member is a compression spring.

5. A system for reducing a spinal rod comprising:
a rotation shaft configured to couple with a rod reducer, the rotation shaft including:
a body including a threaded portion disposed along an inner surface of a longitudinal throughhole;
a rod including a distal end and threads configured to engage the threaded portion;
a first anvil coupled to the distal end of the threaded rod;
a linkage coupled to the first anvil; and
a biasing member partially disposed about the linkage distal of the first anvil, wherein rotation of the threaded rod translates into linear movement of the linkage relative to the body; and
a rod reducer configured to couple with a bone screw and reduce a spinal rod therein, the rod reducer including:
a housing having a shaft slidably disposed therethrough; the shaft defining a head at a proximal end thereof configured to engage the linkage of the rotation shaft;
a second anvil coupled to a distal end of the shaft, the second anvil configured to engage a spinal rod; and
a first arm member and a second arm member operably coupled to the second anvil and the housing, first and second arm members transitionable between a first orientation, coupled with a bone screw, and a second orientation, uncoupled from a bone screw, wherein proximal and distal translation of the shaft with respect to the housing transitions first and second arm members between the first and second orientations.

6. The system of claim 5, wherein the rotation shaft further includes a button assembly configured to selectively fix the rod reducer thereto, the button assembly disposed within a receiving cavity of the body and includes:
a latch including a hooked portion, an elongated throughhole, and a post;
a button disposed about the post and configured to transition the latch between an engaged configuration and a disengaged configuration; and
a biasing element disposed about the post and configured to bias the button towards one of the engaged or disengaged configurations.

7. The system of claim 6, wherein the hooked portion of the latch is configured to engage a recess of the rod reducer with the button assembly in the engaged configuration, such that longitudinal translation of the body with respect to the rod reducer is thereby inhibited.

8. The system of claim 5, further including a plurality of rotation shafts and a plurality of rod reducers.

* * * * *